US011078534B2

(12) United States Patent
Nierth et al.

(10) Patent No.: US 11,078,534 B2
(45) Date of Patent: Aug. 3, 2021

(54) PHOTOCLEAVABLE NUCLEOTIDE REAGENTS WITH HIGH STABILITY

(71) Applicant: Roche Molecular Systems, Inc., Pleasanton, CA (US)

(72) Inventors: Alexander Nierth, Dublin, CA (US); Hannes Kuchelmeister, Munich (DE); Concordio Anacleto, Dublin, CA (US); Amar Gupta, Danville, CA (US); Dieter Heindl, Munich (DE); Igor Kozlov, Danville, CA (US); Christian Wellner, Penzberg (DE); Stephen Gordon Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 339 days.

(21) Appl. No.: 16/199,757

(22) Filed: Nov. 26, 2018

(65) Prior Publication Data

US 2019/0161797 A1 May 30, 2019

Related U.S. Application Data

(60) Provisional application No. 62/590,972, filed on Nov. 27, 2017.

(51) Int. Cl.
| | | |
|---|---|---|
| C12Q 1/68 | (2018.01) | |
| C07H 19/10 | (2006.01) | |
| C07H 19/20 | (2006.01) | |
| C07H 21/02 | (2006.01) | |
| C12Q 1/6876 | (2018.01) | |
| C12Q 1/6848 | (2018.01) | |
| C12Q 1/686 | (2018.01) | |

(52) U.S. Cl.
CPC .......... *C12Q 1/6876* (2013.01); *C07H 19/10* (2013.01); *C07H 19/20* (2013.01); *C07H 21/02* (2013.01); *C12Q 1/686* (2013.01); *C12Q 1/6848* (2013.01)

(58) Field of Classification Search
CPC ........ C07H 19/20; C07H 19/10; C07H 21/02; C12Q 1/686; C12Q 1/6876; C12Q 1/6848
See application file for complete search history.

(56) References Cited

U.S. PATENT DOCUMENTS

| | | |
|---|---|---|
| 7,598,019 B2 | 10/2009 | Steiner et al. |
| 2005/0170281 A1 | 8/2005 | Stengele |
| 2016/0138092 A1 | 5/2016 | Johnson et al. |

FOREIGN PATENT DOCUMENTS

| | | |
|---|---|---|
| WO | 2017156218 A1 | 9/2017 |

OTHER PUBLICATIONS

Stratagene Catalog p. 39. (Year: 1988).*
International Search Report and Written Opinion dated Jan. 23, 2019 in Application No. PCT/EP2018/082692, 10 pages.

(Continued)

Primary Examiner — Jezia Riley
(74) Attorney, Agent, or Firm — David J. Chang

(57) ABSTRACT

The present invention provides for stable nucleotide reagents used for nucleic acid amplification by PCR and RT-PCR (Reverse Transcriptase-PCR) that comprises modified nucleoside triphosphates. The present invention also provides for methods for using the modified nucleoside triphosphates for detecting the presence or absence of a target nucleic acid sequence in a sample in an amplification reaction.

7 Claims, 6 Drawing Sheets

(56) References Cited

OTHER PUBLICATIONS

Tang, X., et al., Caged nucleotides/nucleosides and their photo-chemical biology, Organic & Biomolecular Chemistry, Jan. 1, 2013, pp. 7814-7824, vol. 11, No. 45.

Kretschy, N. et al., "Next-Generation o-Nitrobenzyl Photolabile Groups for Light-Directed Chemistry and Microarray Synthesis", Angew. Chem. Int. Ed., 2015, 54, 8555-8559.

* cited by examiner

PHOTOCLEAVABLE NUCLEOTIDE REAGENTS WITH HIGH STABILITY

CROSS REFERENCE TO RELATED APPLICATIONS

This application claims the benefit of priority of U.S. Provisional Patent Application Ser. No. 62/590,972, filed Nov. 27, 2017, which is incorporated herein by reference in its entirety.

FIELD OF THE INVENTION

The present invention provides for stable nucleotide reagents, methods for their preparation, methods for their use, and kits comprising them. The nucleotide reagents are useful in many recombinant DNA techniques, especially nucleic acid amplification by the polymerase chain reaction (PCR).

BACKGROUND OF THE INVENTION

Nucleic acid amplification reagents are typically comprised of temperature sensitive components, and therefore must often be stored and shipped at temperatures well below ambient temperature. This is particularly the case with deoxynucleoside triphosphates or their ribonucleoside triphosphate analogs. These reagents are prone to degradation via loss of consecutive phosphate groups from the termini, resulting in the formation of nucleoside diphosphates and monophosphates, both of which are no longer active as substrates of nucleic acid polymerases. The stability of nucleoside polyphosphates can be improved substantially by esterifying the terminal phosphates. For example, γ-methyl-dNTP analogs were completely stable under conditions of heat stress that were sufficient to completely degrade normal dNTPs. However, esterification of the terminal phosphate can have a negative effect on the ability of these nucleotides to serve as effective substrates for certain polymerase enzymes. A need exists for having nucleoside triphsosphates that are both thermally stable and are inactive initially as substrates but are readily activated by simple steps.

BRIEF SUMMARY OF THE INVENTION

The present invention provides for thermally stable nucleotide reagents used for nucleic acid amplification by PCR and RT-PCR (Reverse Transcriptase-PCR) that comprises modified nucleoside polyphosphates having a photocleavable moiety. The present invention also provides for methods for using the modified nucleoside triphosphates for detecting the presence or absence of a target nucleic acid sequence in a sample in an amplification reaction.

Therefore in one aspect, the present invention involves a method of detecting the presence or absence of a target nucleic acid sequence in a sample comprising performing an amplifying step comprising contacting the sample with amplification reagents to produce an amplification product if the target nucleic acid sequence is present in the sample, and detecting the amplification product, wherein the amplification reagents comprise a modified nucleoside triphosphate having a photocleavable moiety and having a structure of:

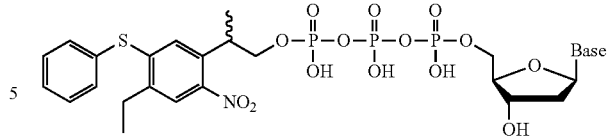

where Base is a purine or pyrimidine base, or an analog. In one embodiment, prior to the amplifying step, the modified nucleoside polyphosphate is irradiated with light having a wavelength capable of cleaving the photocleavable moiety.

In another aspect, the present invention involves a method of amplifying a target nucleic acid sequence using amplification reagents wherein the amplification reagents comprise a modified nucleoside triphosphate having photocleavable moiety and having a structure of:

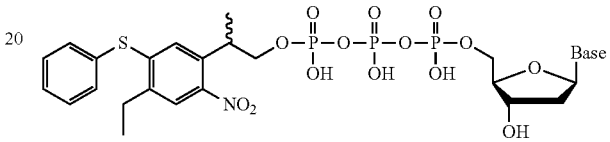

where Base is a purine or pyrimidine base, or an analog. In one embodiment, prior to amplifying, the modified nucleoside triphosphate is irradiated with light having a wavelength capable of cleaving the photocleavable moiety.

In another aspect, the present invention involves a method of reducing or preventing non-specific amplification of nucleic acid during an amplification reaction comprising providing amplification reagents that are used to amplify a target nucleic acid, wherein the amplification reagents comprise a modified nucleoside triphosphate having a photocleavable moiety and having a structure of:

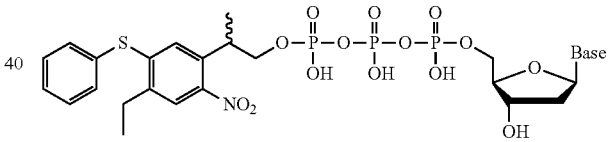

where Base is a purine or pyrimidine base or an analog. In one embodiment, prior to amplifying, the modified nucleoside triphosphate is irradiated with light having a wavelength capable of cleaving the photocleavable moiety.

In another aspect, the present invention involves a composition comprising a modified nucleoside triphosphate having photocleavable moiety and having a structure of:

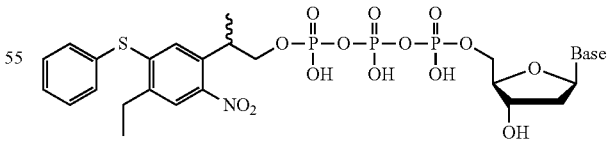

where Base is a purine or pyrimidine base, or an analog. In one embodiment, the modified nucleoside triphosphate is characterized by having greater thermostability compared to an unmodified nucleoside triphosphate.

In yet another aspect, the present invention provides for a kit comprising the modified nucleoside triphosphate and further comprising reagents necessary for performing an amplification reaction.

The embodiments and advantages of the invention are described in more detail in the Detailed Description of the Invention and in the Figures.

DETAILED DESCRIPTION OF THE INVENTION

Figure 1:
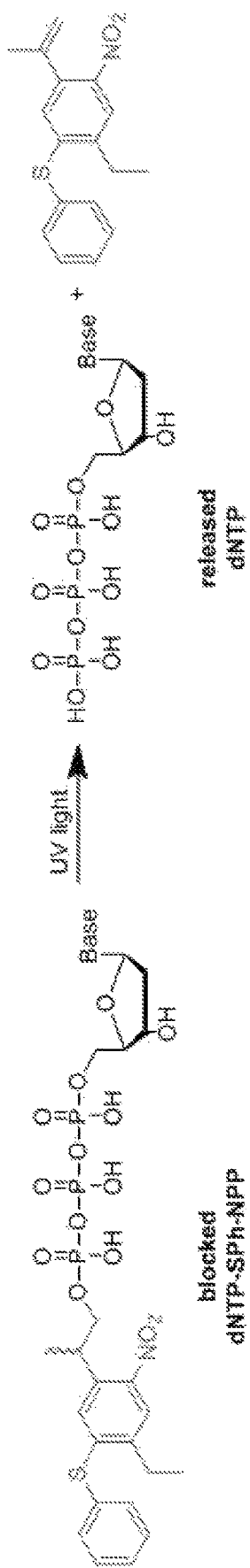
FIG. 1 shows the structure and general concept of the photocleavable nucleoside triphosphate, thiophenyl o-nitrophenylpropyl dNTP.

The present invention provides for thermally stable modified nucleoside triphosphate having a photocleavable moiety, methods for their preparation, methods for their use, and kits comprising them. These thermally stable modified nucleoside triphosphates are useful in many recombinant DNA techniques, especially nucleic acid amplification by the polymerase chain reaction (PCR).

Definitions

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "ambient temperature" refers to the temperature of the surrounding and is synonymous with "room temperature" when referring to the temperature of a temperature-controlled indoor building. Typically, ambient temperature refers to a temperature range of between 15° C. and 25° C. although slightly cooler or warmer temperatures may still be considered within the range of ambient temperature.

The term "photocleavable moiety" that is used herein has several synonymous words in the literature and can also be referred to as "photoremovable groups", "photoblocking groups", "phototriggers", "caged compounds". "photolabile groups", and other similar terms. One advantage of employing a photocleavable moiety is the ability to control reactions by temporally blocking or masking its function with high selectivity. The photocleavable moiety can be selected to be cleaved, i.e., decoupled, from the nucleoside triphosphate with a light of a certain wavelength, for example a wavelength of between about 200 nm to about 450 nm, e.g., between about 200 nm to about 300 nm, or e.g., between about 280 nm to about 315 nm, or e.g., between about 300 nm to about 400 nm, or e.g., between about 315 nm to about 415 nm. The term "about" in the context of a stated wavelength may include exactly the stated wavelength, and also include a wavelength having 1 nm, 2 nm, 3 nm, 4 nm, or 5 nm, plus or minus the stated wavelength. Thus, when a light of appropriate wavelength is introduced, e.g., by shining or flashing, to the modified nucleoside triphosphate, the photocleavable moiety is cleaved which removes the steric or other interferences from processing by nucleic acid polymerases. The introduction of the light can be manual or automated. Once the light is introduced and the photocleavable moieties are removed, the restored nucleoside triphosphate can become a substrate for the polymerase during the PCR reaction.

"Recombinant", as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by restriction endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

"Amplification reagents" are chemical or biochemical components that enable the amplification of nucleic acids. Such reagents comprise, but are not limited to, nucleic acid polymerases, buffers, mononucleotides such as nucleoside triphosphates, oligonucleotides e.g. as oligonucleotide primers, salts and their respective solutions, detection probes, dyes, and more.

As is known in the art, a "nucleoside" is a base-sugar combination. The base portion of the nucleoside is normally a heterocyclic base. The two most common classes of such heterocyclic bases are purines and pyrimidines.

"Nucleotides" are nucleosides that further include a phosphate group covalently linked to the sugar portion of the nucleoside. For those nucleosides that include a pentofuranosyl sugar, the phosphate group can be linked to either the 2'-, 3'- or 5'-hydroxyl moiety of the sugar. A nucleotide is the monomeric unit of an "oligonucleotide", which can be more generally denoted as an "oligomeric compound", or a "polynucleotide", more generally denoted as a "polymeric compound". Another general expression for the aforementioned is deoxyribonucleic acid (DNA) and ribonucleic acid (RNA).

An "oligomeric compound" is a compound consisting of "monomeric units" which may be nucleotides alone or non-natural compounds (see below), more specifically modified nucleotides (or nucleotide analogs) or non-nucleotide compounds, alone or combinations thereof.

"Oligonucleotides" and "modified oligonucleotides" (or "oligonucleotide analogs") are subgroups of oligomeric compounds. The term "oligonucleotide" refers to components formed from a plurality of nucleotides as their monomeric units. The phosphate groups are commonly referred to as forming the internucleoside backbone of the oligonucleotide. The normal linkage or backbone of RNA and DNA is a 3' to 5' phosphodiester linkage. Oligonucleotides and modified oligonucleotides (see below) useful for the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang S. A. et al., Methods in Enzymology 68 (1979) 90-98, the phosphodiester method disclosed by Brown E. L., et al., Methods in Enzymology 68 (1979) 109-151, the phosphoramidite method disclosed in Beaucage et al., Tetrahedron Letters 22 (1981) 1859, the H-phosphonate method disclosed in Garegg et al., Chem. Ser. 25 (1985) 280-282 and the solid support method disclosed in U.S. Pat. No. 4,458,066.

In the process described above, the oligonucleotides may be chemically modified, i.e. the primer and/or the probe comprise of a modified nucleotide or a non-nucleotide compound. The probe or the primer is then a modified oligonucleotide.

"Modified nucleotides" (or "nucleotide analogs") differ from a natural nucleotide by some modification but still consist of a base, a pentofuranosyl sugar, a phosphate portion, base-like, pentofuranosyl sugar-like and phosphate-like portion or combinations thereof. For example, a label may be attached to the base portion of a nucleotide whereby a modified nucleotide is obtained. A natural base in a nucleotide may also be replaced by e.g. a 7-deazapurine whereby a modified nucleotide is obtained as well.

A "modified oligonucleotide" (or "oligonucleotide analog"), belonging to another specific subgroup of oligomeric compounds, possesses one or more nucleotides and one or more modified nucleotides as monomeric units. Thus, the term "modified oligonucleotide" (or "oligonucleotide analog") refers to structures that function in a manner substantially similar to oligonucleotides and can be used interchangeably in the context of the present invention. From a synthetical point of view, a modified oligonucleotide (or an oligonucleotide analog) can for example be made by chemical modification of oligonucleotides by appropriate modification of the phosphate backbone, ribose unit or the nucleotide bases (Uhlmann and Peyman, Chem. Rev. 90 (1990) 543; Verma S., and Eckstein F., Annu. Rev. Biochem. 67 (1998) 99-134). Representative modifications include phosphorothioate, phosphorodithioate, methyl phosphonate, phosphotriester or phosphoramidate inter-nucleoside linkages in place of phosphodiester internucleoside linkages; deaza- or azapurines and -pyrimidines in place of natural purine and pyrimidine bases, pyrimidine bases having substituent groups at the 5 or 6 position; purine bases having altered substituent groups at the 2, 6 or 8 positions or 7 position as 7-deazapurines; bases carrying alkyl-, alkenyl-, alkinyl or aryl-moieties, e.g. lower alkyl groups such as methyl, ethyl, propyl, butyl, tert-butyl, pentyl, hexyl, heptyl, octyl, nonyl, decyl, or aryl groups like phenyl, benzyl, naphtyl; sugars having substituent groups at, for example, their 2' position; or carbocyclic or acyclic sugar analogs. Other modifications are known to those skilled in the art. Such modified oligonucleotides (or oligonucleotide analogs) are best described as being functionally interchangeable with, yet structurally different from, natural oligonucleotides. In more detail, exemplary modifications are disclosed in Verma S., and Eckstein F., Annu. Rev. Biochem. 67 (1998) 99-134 or WO 02/12263. In addition, modification can be made wherein nucleoside units are joined via groups that substitute for the internucleoside phosphate or sugar phosphate linkages. Such linkages include those disclosed in Verma S., and Eckstein F., Annu. Rev. Biochem. 67 (1998) 99-134. When other than phosphate linkages are utilized to link the nucleoside units, such structures have also been described as "oligonucleosides".

A "nucleic acid" as well as the "target nucleic acid" is a polymeric compound of nucleotides as known to the expert skilled in the art. "Target nucleic acid" is used herein to denote a nucleic acid in a sample which should be analyzed. i.e. the presence, non-presence and/or amount thereof in a sample should be determined.

The term "primer" is used herein as known to the expert skilled in the art and refers to oligomeric compounds, primarily to oligonucleotides, but also to modified oligonucleotides that are able to prime DNA synthesis by a template-dependent DNA polymerase, i.e. the 3'-end of the e.g. primer provides a free 3'—OH group whereto further nucleotides may be attached by a template-dependent DNA polymerase establishing 3'- to 5'-phosphodiester linkage whereby deoxynucleoside triphosphates are used and whereby pyrophosphate is released.

A "probe" also denotes a natural or modified oligonucleotide. As known in the art, a probe serves the purpose to detect an analyte or amplificate. In the case of the process described above, probes can be used to detect the amplificates of the target nucleic acids. For this purpose, probes typically carry labels.

"Labels", often referred to as "reporter groups", are generally groups that make a nucleic acid, in particular oligonucleotides or modified oligonucleotides, as well as any nucleic acids bound thereto distinguishable from the remainder of the sample (nucleic acids having attached a label can also be termed labeled nucleic acid binding compounds, labeled probes or just probes). Exemplary labels are fluorescent labels, which are e.g. fluorescent dyes such as a fluorescein dye, a rhodamine dye, a cyanine dye, and a coumarin dye. Exemplary fluorescent dyes are FAM, HEX, JA270, CAL635, Coumarin343, Quasar705, CyanS00, CY5.5, LC-Red 640, LC-Red 705.

Any primer and/or probe may be chemically modified, i.e. the primer and/or the probe comprise of a modified nucleotide or a non-nucleotide compound. The probe or the primer is then a modified oligonucleotide.

A method of nucleic acid amplification is the Polymerase Chain Reaction (PCR) which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer can be single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have e.g. been isolated from *Thermnus flavus, T. ruber, T. thermophilus, T. aquaticus, T. lacteus, T. ruben, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec. to 9 min. In order to not expose the respective polymerase like e.g. the Z05 DNA Polymerase to such high temperatures for too long and thus risking a loss of functional enzyme, it can be preferred to use short denaturation steps.

If the double-stranded template nucleic acid is denatured by heat, the reaction mixture is allowed to cool to a temperature that promotes annealing of each primer to its target sequence on the target nucleic acids.

The temperature for annealing can be from about 35° C. to about 70° C., or about 45° C. to about 65° C., or about 50° C. to about 60° C., or about 55° C. to about 58° C. Annealing times can be from about 10 sec. to about 1 min. (e.g., about 20 sec. to about 50 sec.; about 30 sec. to about 40 sec.). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic mutations which should also be detected. On the other hand, relatively high annealing temperatures bear the advantage of providing higher specificity, since towards higher temperatures the probability of primer binding to not exactly matching target sequences continuously decreases. In order to benefit from both phenomena, in some embodiments of the invention the process described above comprises of annealing at different temperatures, for example first at a lower, then at a higher temperature. If, e.g., a first incubation takes place at 55° C. for about 5 cycles, non-exactly matching target sequences may be (pre-)amplified. This can be followed e.g. by about 45 cycles at 58° C., providing for higher specificity throughout the major part of the experiment. This way, potentially important genetic mutations are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° C. to 80° C. (e.g., about 50° C. to about 70° C.; about 65° C.). Extension times can be from about 10 sec. to about 5 min., or about 15 sec to 2 min., or about 20 sec. to about 1 min., or about 25 sec. to about 35 sec. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) can be repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

PCR can be carried out in which the steps of annealing and extension are performed in the same step (one-step PCR) or, as described above, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, the one-step PCR reduces the overall complexity of the respective assay.

In general, shorter times for the overall amplification can be preferred, as the time-to-result is reduced and leads to a possible earlier diagnosis.

Other nucleic acid amplification methods to be used comprise the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic, 1 (1991) 5-16); Gap-LCR (WO 90/01069); Repair Chain Reaction (EP 0439182 A2); 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808); and NASBA (U.S. Pat. No. 5,130,238). Further, there are strand displacement amplification (SDA), transcription mediated amplification (TMA), and Qb-amplification (for a review see e.g. Whelen A. C. and Persing D. H., Annu. Rev. Microbiol. 50 (1996) 349-373; Abramson R. D. and Myers T. W., Curr. Opin. Biotechnol. 4 (1993) 41-47).

The term "Cp value" or "crossing point" value refers to a value that allows quantification of input target nucleic acids. The Cp value can be determined according to the second-derivative maximum method (Van Luu-The, et al., "Improved real-time RT-PCR method for high-throughput measurements using second derivative calculation and double correction," BioTechniques, Vol. 38, No. 2, February 2005, pp. 287-293). In the second derivative method, a Cp corresponds to the first peak of a second derivative curve. This peak corresponds to the beginning of a log-linear phase. The second derivative method calculates a second derivative value of the real-time fluorescence intensity curve, and only one value is obtained. The original Cp method is based on a locally defined, differentiable approximation of the intensity values, e.g., by a polynomial function. Then the third derivative is computed. The Cp value is the smallest root of the third derivative. The Cp can also be determined using the fit point method, in which the Cp is determined by the intersection of a parallel to the threshold line in the log-linear region (Van Luu-The, el al., BioTechniques, Vol. 38, No. 2, February 2005, pp. 287-293). The Cp value provided by the LightCycler instrument offered by Roche is calculated according to the second-derivative maximum method.

The term "PCR efficiency" refers to an indication of cycle to cycle amplification efficiency. PCR efficiency is calculated for each condition using the equation: % PCR efficiency=$(10^{(-slope)}-1) \times 100$, wherein the slope was calculated by linear regression with the log copy number plotted on the y-axis and Cp plotted on the x-axis. PCR efficiency can be measured using a perfectly matched or mismatched primer template.

The term "FRET" or "fluorescent resonance energy transfer" or "Förster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include Black Hole Quenchers™ (BHQ), (Biosearch Technologies, Inc., Novato, Calif.), Iowa Black™ (Integrated DNA Tech., Inc., Coralville, Iowa), and BlackBerry™ Quencher 650 (BBQ-650) (Berry & Assoc., Dexter, Mich.).

The methods set out above can be based on Fluorescence Resonance Energy Transfer (FRET) between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, detection includes exciting the sample at a wavelength absorbed by the donor fluorescent moiety and visualizing and/or measuring the wavelength emitted by the corresponding acceptor fluorescent moiety. In the process according to the invention, detection can be followed by quantitating the FRET. For example, detection is performed after each cycling step. For example, detection is performed in real time. By using commercially available real-time PCR instrumentation (e.g., LightCycler™ or TaqMan®), PCR amplification and detection of the amplification product can be combined in a single closed cuvette with significantly reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The following patent applications describe real-time PCR as used in the LightCycler® technology: WO 97/46707, WO 97/46714 and WO 97/46712. The LightCycler® instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TaqMan® technology utilizes a single-stranded hybridization probe labeled with two chromophor moieties. When a first fluorescent moiety is excited with light of a suitable wavelength, the absorbed energy is transferred to a second chromophor according to the principles of FRET. Typical fluorescent dyes used in this format are for example, among others, FAM, HEX, CY5, JA270, Cyan and CY5.5. The second chromophore is generally a quencher molecule. During the annealing step of the PCR reaction, the labeled hybridization probe binds to the target nucleic acid (i.e., the amplification product) and is degraded by the 5' to 3' exonuclease activity of the Taq or another suitable polymerase as known by the skilled artisan, such as a Z05 polymerase variant, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

As an alternative to FRET, an amplification product can be detected using a double-stranded DNA binding dye such as a fluorescent DNA binding dye (e.g., SYBRGREEN 1®, or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g. a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, in a method according to the invention is the method described above using FRET, wherein said probes comprise a nucleic acid sequence that permits secondary structure formation, wherein said secondary structure formation results in spatial proximity between said first and second fluorescent moiety.

Efficient FRET can only take place when the fluorescent moieties are in local proximity and when the emission spectrum of the donor fluorescent moiety overlaps with the absorption spectrum of the acceptor fluorescent moiety.

Thus, in an embodiment, said donor and acceptor fluorescent moieties are within no more than 5 nucleotides of each other on said probe. In a further embodiment, said acceptor fluorescent moiety is a quencher.

As described above, in the TaqMan® format, during the annealing step of the PCR reaction, the labeled hybridization probe binds to the target nucleic acid (i.e., the amplification product) and is degraded by the 5'- to 3'-exonuclease activity of the Taq or another suitable polymerase as known by the skilled artisan, such as a Z05 polymerase variant, during the subsequent elongation phase. Thus, in an embodiment, in the process described above, amplification employs a polymerase enzyme having 5'- to 3'-exonuclease activity.

It is further advantageous to carefully select the length of the amplicon that is yielded as a result of the process described above. Generally, relatively short amplicons increase the efficiency of the amplification reaction. Thus, an aspect of the invention is the process described above, wherein the amplified fragments comprise up to 450 bases, up to 300 bases, up to 200 bases, or up to 150 bases.

A "sequence" is the primary structure of a nucleic acid, i.e. the specific arrangement of the single nucleobases of which the respective nucleic acids consists. It has to be understood that the term "sequence" does not denote a specific type of nucleic acid such as RNA or DNA, but applies to both as well as to other types of nucleic acids such as e.g. peptide nucleic acid (PNA) or others. Where nucleobases correspond to each other, particularly in the case of uracil (present in RNA) and thymine (present in DNA), these bases can be considered equivalent between RNA and DNA sequences, as known in the pertinent art.

Clinically relevant nucleic acids are often DNA which can be derived from DNA viruses like e.g. Hepatitis B Virus (HBV), Cytomegalovirus (CMV) and others, or bacteria like e.g. *Chlamydia trachomatis* (CT), *Neisseria gonorrhoeae* (NG) and others. In such cases, it can be advantageous to use an internal control nucleic acid consisting of DNA, in order to reflect the target nucleic acids properties. The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants. The cells can be prokaryotic or eukaryotic.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, positive retroregulatory elements (see U.S. Pat. No. 4,666,848, incorporated herein by reference), and possibly other sequences. Eucaryotic cells are known to utilize promoters, polyadenylation signals, and enhancers.

The terms "restriction endonucleases" and "restriction enzymes" refer to enzymes, typically bacterial in origin, which cut double-stranded DNA at or near a specific nucleotide sequence.

Families of amino acid residues having similar side chains are defined herein. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine).

The term "reagent solution" is any solution containing at least one reagent needed or used for PCR purposes. Most typical ingredients are polymerase, nucleotides, primers, divalent metal ions (such as magnesium), salts, pH buffering agents, nucleoside triphosphates (NTPs) or deoxynucleoside triphosphates (dNTPs), one or more probes, fluorescent dyes (may be attached to probe), nucleic acid binding agents, and one or more nucleic acid templates. The reagent may also be another polymerase reaction additive, which has an influence on the polymerase reaction or its monitoring.

The term "mastermix" refers to a mixture of all or most of the ingredients or factors necessary for PCR to occur, and in some cases, all except for the template and primers which are sample and amplicon specific. Commercially available mastermixes are usually concentrated solutions. A mastermix may contain all the reagents common to multiple samples, but it may also be constructed for one sample only. Using mastermixes helps to reduce pipetting errors and variations between samples due to differences between pipetted volumes.

The term "thermostable polymerase" refers to an enzyme that is stable to heat, is heat resistant and retains sufficient activity to effect subsequent primer extension reactions after being subjected to the elevated temperatures for the time necessary to denature double-stranded nucleic acids. Heating conditions necessary for nucleic acid denaturation are well known in the art and are exemplified in U.S. Pat. Nos. 4,965,188 and 4,889,818, which are incorporated herein by reference. As used herein, a thermostable polymerase is suitable for use in a temperature cycling reaction such as PCR. The examples of thermostable nucleic acid polymerases include *Thermus aquaticus* Taq DNA polymerase,

*Thermus* sp. Z05S polymerase, *Thermus flavus* polymerase, *Thermotoga maritimna* polymerases, such as TMA-25 and TMA-30 polymerases, Tth DNA polymerase, and the like.

A "polymerase with reverse transcriptase activity" is a nucleic acid polymerase capable of synthesizing DNA based on an RNA template. It is also capable of replicating a single or double-stranded DNA once the RNA has been reverse transcribed into a single strand cDNA. In an embodiment of the invention, the polymerase with reverse transcriptase activity is thermostable.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step. In a non-homogeneous RT/PCR reaction, following reverse transcription and prior to amplification one or more of the reaction components such as the amplification reagents are e.g. adjusted, added, or diluted, for which the reaction vessel has to be opened, or at least its contents have to be manipulated. Both homogeneous and non-homogeneous embodiments are comprised by the scope of the invention.

Reverse transcription is an important step in an RT/PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, e.g. in the case of the possible presence of unknown or rare substrains or subspecies of organisms in the fluid sample.

In order to benefit from both advantages described above, i.e. the reduction of secondary structures and the reverse transcription of templates with mismatches, the RT incubation can be carried out at more than one different temperature.

Therefore, an aspect of the invention is the process described above, wherein said incubation of the polymerase with reverse transcriptase activity is carried out at different temperatures from 30° C. to 75° C., or from 45° C. to 70° C., or from 55° C. to 65° C.

As a further important aspect of reverse transcription, long RT steps can damage the DNA templates that may be present in the fluid sample. If the fluid sample contains both RNA and DNA species, it is thus favorable to keep the duration of the RT steps as short as possible, but at the same time ensuring the synthesis of sufficient amounts of cDNA for the subsequent amplification and optional detection of amplificates.

Thus, an aspect of the invention is the process described above, wherein the period of time for incubation of the polymerase with reverse transcriptase activity is up to 30 min., 20 min., 15 min., 12.5 min., 10 min., 5 min., or 1 min.

A further aspect of the invention is the process described above, wherein the polymerase with reverse transcriptase activity and comprising a sequence variation is selected from the group consisting of
   a) a CS5 DNA polymerase
   b) a CS6 DNA polymerase
   c) a *Thermotoga maritima* DNA polymerase
   d) a *Thermus aquaticus* DNA polymerase
   e) a *Thermus thermophilus* DNA polymerase
   f) a *Thermus flavus* DNA polymerase
   g) a *Thermus filiformis* DNA polymerase
   h) a *Thermnus* sp. sps17 DNA polymerase
   i) a *Thermus* sp. Z05 DNA polymerase
   j) a *Thermotoga neapolitana* DNA polymerase
   k) a *Termosipho africanus* DNA polymerase
   l) a *Thermus caldophilus* DNA polymerase Particularly suitable for these requirements are enzymes carrying a sequence variation in the polymerase domain that enhances their reverse transcription efficiency in terms of a faster extension rate.

Therefore, in the process described above, wherein the polymerase with reverse transcriptase activity is a polymerase variant with improved nucleic acid extension rate and/or an improved reverse transcriptase activity relative to the respective wildtype polymerase.

In an embodiment, in the process described above, the polymerase with reverse transcriptase activity is a polymerase variant with improved reverse transcriptase activity relative to the respective wildtype polymerase.

Polymerases carrying single sequence variations that render them particularly useful are disclosed in WO 2008/046612. In particular, polymerases to be used can be sequence modified DNA polymerases comprising at least the following motif in the polymerase domain:

T-G-R-L-S-S-Xb7-Xb8-P-N-L-Q-N; wherein Xb7 is an amino acid selected from S or T and wherein Xb8 is an amino acid selected from G, T, R, K, or L, wherein the polymerase comprises 3'-5' exonuclease activity and has an improved nucleic acid extension rate and/or an improved reverse transcription efficiency relative to the wildtype DNA polymerase, wherein in said wildtype DNA polymerase Xb8 is an amino acid selected from D, E or N.

One example are variants of the thermostable DNA polymerase from *Thermus* species Z05 (described e.g. in U.S. Pat. No. 5,455,170), said sequence variations in the polymerase domain as compared with the respective wildtype enzyme Z05. An embodiment for the method according to the invention is a Z05 DNA polymerase variant wherein the amino acid at position 580 is selected from the group consisting of G, T, R, K and L.

For reverse transcription using a thermostable polymerase, $Mn^{2+}$ can be the divalent cation and is typically included as a salt, for example, manganese chloride ($MnCl_2$), manganese acetate [$Mn(OAc)_2$], or manganese sulfate ($MnSO_4$). If $MnCl_2$ is included in a reaction containing 50 mM Tricine buffer, for example, the $MnCl_2$ is generally present at a concentration of 0.5-7.0 mM; 2.5-3.5 mM is generally present when 200 µM of each dGTP, dATP, dUTP, and dCTP are utilized.

A "modified" thermostable polymerase refers to a polymerase in which at least one monomer differs from the reference sequence, such as a native or wild-type form of the polymerase or another modified form of the polymerase.

Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified thermostable polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "thermoactive polymerase" refers to an enzyme that is active at the elevated temperatures necessary to ensure specific priming and primer extension (e.g., 55-80° C.).

The terms "peptide," "polypeptide," and "protein" are used interchangeably. The terms "nucleic acid" and "polynucleotide" are used interchangeably. Amino acid sequences are written from amino terminus to carboxy terminus, unless otherwise indicated. Single-stranded nucleic acid sequences are written 5' to 3', unless otherwise indicated. The top strand of a double-stranded nucleic acid sequence is written 5' to 3', and the bottom strand is written 3' to 5', unless otherwise indicated.

Nucleic acid amplification reagents are typically comprised of temperature sensitive components, and therefore must often be stored and shipped at temperatures well below ambient. This is particularly the case with deoxynucleoside triphosphates or their ribonucleoside analogs. These reagents are prone to degradation via loss of consecutive phosphate groups from the terminii, resulting in the formation of nucleoside diphosphates and monophosphates, both of which are no longer active as polymerase substrates.

The stability of nucleoside polyphosphates can be improved quite substantially by esterifying the terminal phosphates. For example, γ-methyl-dNTP analogs were completely stable under conditions of heats stress that were sufficient to completely degrade normal dNTPs. However, esterification of the terminal phosphate can have a negative effect on the ability of nucleotides to serve as effective substrates for certain polymerase enzymes.

The present invention describes improved photocleavable ("caged") nucleoside triphosphates (dNTPs). Installing the thiophenyl o-nitrophenylpropyl group (SPh-NPP) on the terminal phosphate of triphosphates stabilizes dNTPs against slow degradation through hydrolysis. Moreover, the SPh-NPP moiety prevents processing by enzymes such as polymerases. Irradiation of these compounds with UV light irreversibly releases free dNTPs and initiates enzymatic reaction ("Photo-start PCR", see FIG. 1). This strategy suppresses the formation of non-specific PCR products, which originates from the residual room temperature activity of the enzyme. In contrast to hot start PCR, in which the enzyme is activated by heat, the reaction herein is controlled via light-triggered release of the dNTP substrate.

Figure 2:
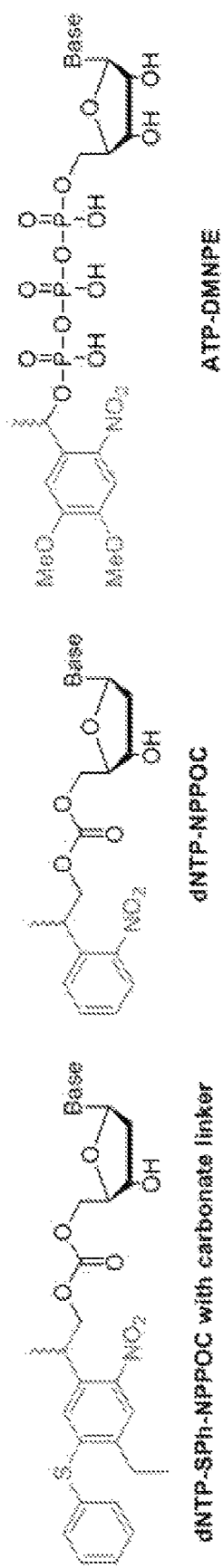
FIG. 2 shows the molecular structures of known photocleavable (d)NTPs.

Attachment of photocleavable groups has been reported by Ghosn, et al., Control of DNA Hybridization with Photocleavable Adducts, *Photochem. Pholobiol.*, 2005, 81:953-959, wherein ester bonds between the phosphate backbone of DNA oligonucleotides and a photocleavable group through the intermediacy of 1-(4,5-dimethoxy-2-nitrophenyl)-ethyl ester (DMNPE). More recently, the thiophenyl extension of the known o-nitrophenyl chromophore was first introduced by Kretschy el al., *Angew. Chem. Int. Ed.*, 2015, 54Z: 8555-8559. Therein, thiophenyl-2-(2-nitrophenyl)-propoxycarbonyl (SPh-NPPOC) was used as a 5'-hydroxyl protecting group on phosphoramidites for photolithographic microarray synthesis. Photolysis of SPh-NPPOC releases a nucleoside, a styrene by-product, and also, due to the carbonate linker, one mole of $CO_2$. The SPh-NPPOC group exhibits a 12-fold increase in photo-deprotection efficiency compared to conventional 2-(2-nitrophenyl)-propoxycarbonyl NPPOC (FIG. 2).

The stability of the SPh-NPP-dNTPs of the present invention is especially suitable for use in locations with limited or no availability of refrigeration. Therefore, the photocleavable dNTPs of the present invention can be stored much longer and at much higher temperatures than "conventional" dNTPs.

While the foregoing invention has been described in some detail for purposes of clarity and understanding, it will be clear to one skilled in the art from a reading of this disclosure that various changes in form and detail can be made without departing from the true scope of the invention. For example, all the compositions and methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The following examples are given to illustrate embodiments of the present invention as it is presently preferred to practice. It will be understood that the examples are illustrative, and that the invention is not be considered as restricted except as indicated in the appended claims.

EXAMPLES

Abbreviations: ACN: acetonitrile; CDI: 1,1'-carbonyldiimidazole; DMF: dimethylformamide: DMSO: dimethylsulfoxide; MeOH: methanol; TBA: tributylammonium; TEA: trimethylamine; TEAA: triethylammonium acetate; THF: tetrahydrofuran.

Example 1: Preparation of thiophenyl o-nitrophenylpropyl dATP (dATP-SPh-NPP)

Figure 3:
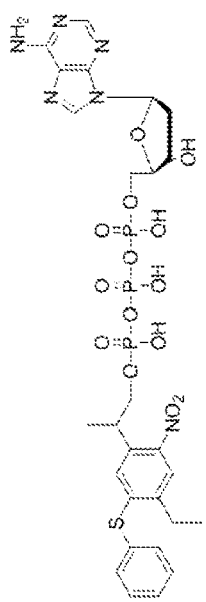
FIG. 3 is a schematic for the prepration of thiphenyl o-nitrophenylpropyl dATP (dATP-SPh-NPP).
Figure 3:
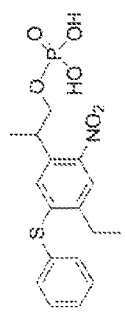
Figure 3:
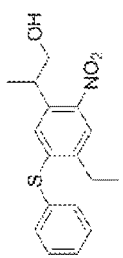

The synthesis of dATP-SPh-NPP is shown schematically on FIG. 3 and is briefly described here. All steps were carried out in the dark. PhSNPP3OH

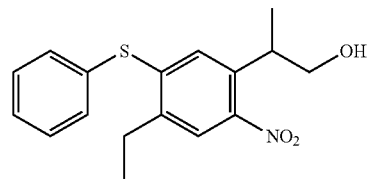 [SMILES: CCc1cc([N+](=O)[O-])c(C(C)CO)cc1Sc1ccccc1]

was dissolved in THF (5 mL, dry) under Ar atmosphere and cooled to 0-4° C. 220 μL TEA (dry) and 127 &L $POCl_3$ were added and the reaction was stirred for 18 h, quenched with water (8 mL) and stirred for 1.5 h. The aqueous phase was extracted three times with ethyl acetate. The combined organic phases were dried over $Na_2SO_4$. The solvent was removed under reduced pressure. The residue was dissolved in ACN/H$_2$O and lyophilized to give 200 mg of PhSNPP3MP

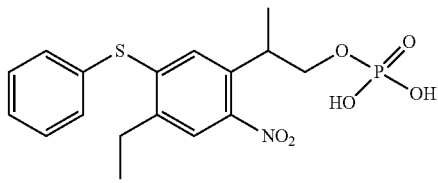 [SMILES: CCc1cc([N+](=O)[O-])c(C(C)COP(=O)(O)O)cc1Sc1ccccc1]

as a sticky resin, which was directly used for the next step. 200 mg of raw PhSNPP3MP were dissolved in 6 mL, DMF (dry), CDI was added and the mixture was stirred for 4 h und dry conditions. Excess CDI was quenched with MeOH and stirred for 30 min. 52 mg MgCl$_2$ and then 2.2 eq TBA-ADP solution were added and the reaction was stirred for 3 days. 0.1 M TEAA buffer (pH 4.1) was added in a 1:1 ratio. Diaion HP20 resin was added, the mixture was stirred for 30 min and filtrated. The filtrate was washed with water and the product was eluted with MeOH. The solvent was then removed in vacuum, the remaining residue was dissolved in water and purified by RP18-HPLC. Product fractions were combined and lyophilized to give PhSNPP3ATP in 51% yield.

Example 2: Stability Studies Using dATP-SPh-NPP

An aqueous mixture was prepared, containing 300 μM dATP-SPh-NPP, 40% DMSO and 1.0 M potassium acetate. For reference another mixture with 300 μM dATP replacing dATP-SPh-NPP was prepared. 150 μL of each mixture were incubated at 65° C. in a Thermoshaker. After 0, 2, 18, 25, and 120 h samples of each solution (20 μL) were analyzed by UPLC-MS (Ultra performance liquid chromatography—mass spectrometry). The peak areas at 260 nm were used to calculate the percentage of starting material and degradation products.

Figure 4:
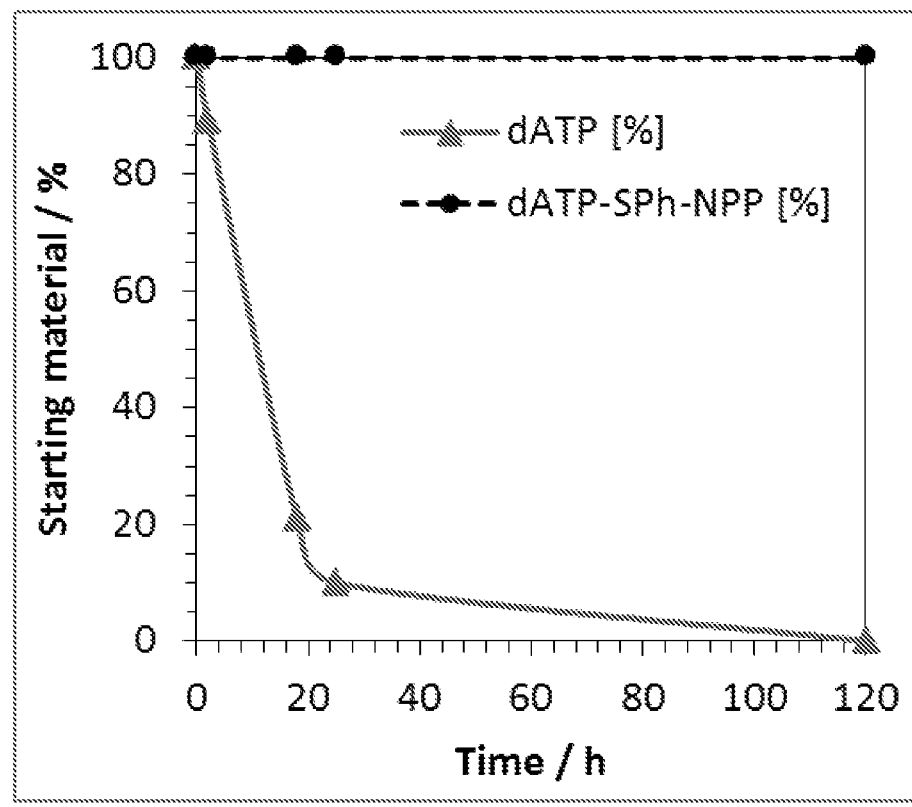
FIG. 4 shows the thermostability of thiophenyl o-nitrophenylpropyl dATP (dATP-SPh-NPP) compared to regular dATP. The samples were exposed to 65° C. for up to 120 h.

Result: Under the conditions employed dATP quickly degraded to the mono- and diphosphates as confirmed by mass spectrometry. dATP-SPh-NPP is significantly more thermostable than dATP and no degradation products were observed for dATP-SPh-NPP at 65° C. for 120 h (FIG. 4).

Example 3: Photocleavage of dATP-SPh-NPP

Two aqueous mixtures of dATP-SPh-NPP and ATP-DMNPE (300 μM each) were prepared in sodium phosphate buffer (100 mM, pH 7.0). Both samples were irradiated simultaneously with light from an UV-LED lamp (InGaN, Quantum well, $\lambda_{max}$=393 nm, 0.18 W/LED) in open vials without shaking or stirring. After 0, 1, 2, 4, 8, and 16 min. the irradiation was shortly paused for sample removal (20 μL) and subsequent UPLC-MS analysis. The peak areas at 260 nm were used to calculate the percentage of starting material and photocleavage products. The molecular identities of the starting materials and cleavage products were confirmed by mass spectrometry.

Figure 5:
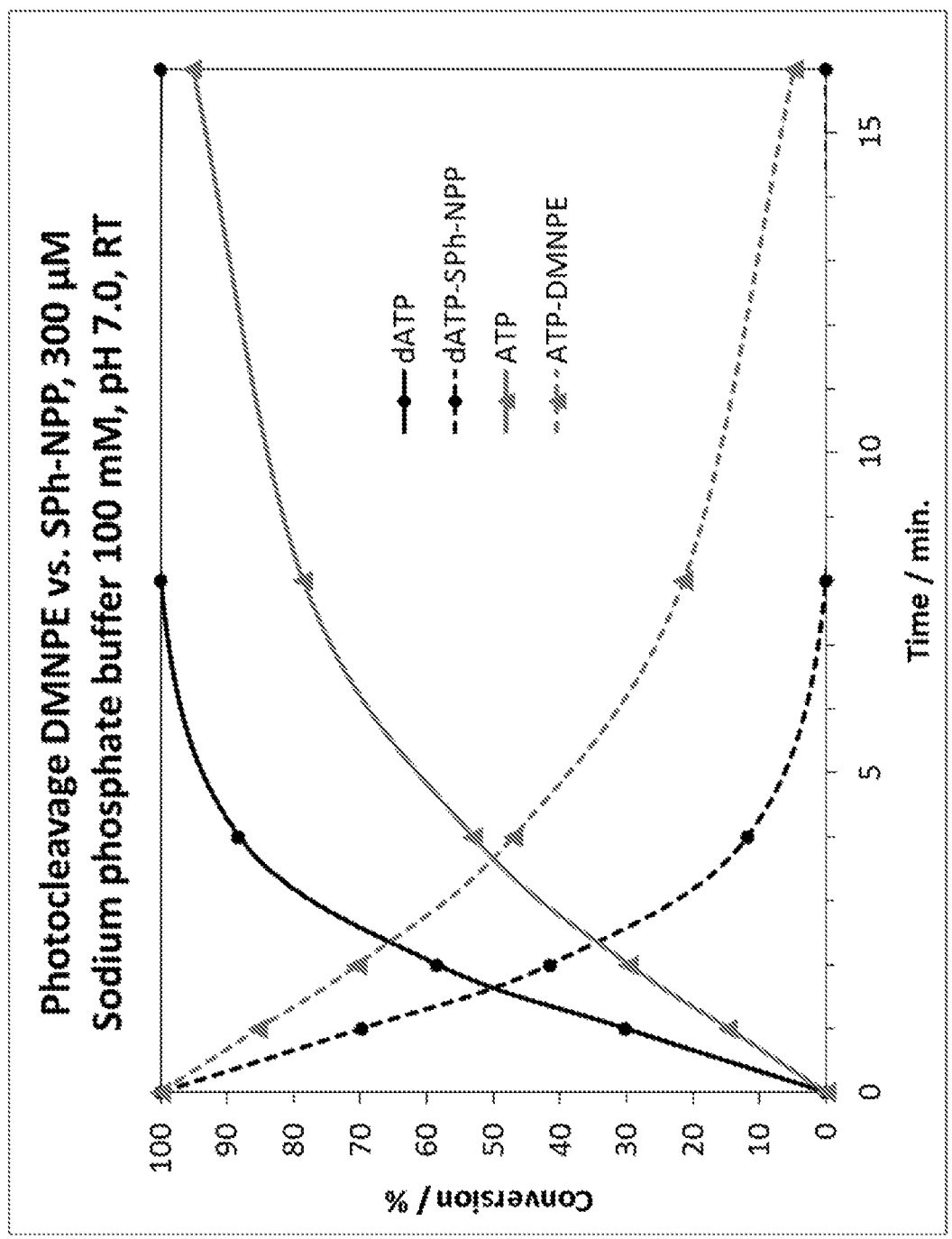
FIG. 5 shows the photocleavage of thiophenyl o-nitrophenylpropyl dATP (dATP-SPh-NPP) compared to DMNPE-ATP, a commercially available photocleavable nucleotide, with LED UV flashlight in 100 mM phosphate buffer, pH 7.0 at room temperature.

Result: More than >90% dATP was released by irradiating dATP-SPh-NPP for 5 minutes, and full cleavage was accomplished in 8 minutes (FIG. 5). Photocleavage of dATP-SPh-NPP is significantly faster than with commercially available ATP-DMNPE (Thermo-Fisher Scientific).

Example 4: Amplification Reactions Using dATP-SPh-NPP

Real-Time PCR (TaqMan® PCR) mixtures with a total volume of 50 μL were prepared by combining three components termed PCR master mixture (20 μL), buffer mixture (20 μL), and dNTP mixture (10 μL). All PCR components were prepared from DEPC water. The PCR master mixture contained tricine buffer (pH 8.2), potassium acetate, glycerol, DMSO, detergent, target DNA (400 cp), polymerase aptamer, probe, primers, SYBR green dye, and polymerase enzyme. The buffer mixture contained manganese acetate (8.3 mM) and imidazole (0, 3.0, or 6.0 mM). The dNTP mixture contained dATP (400 μM), dCTP (400 μM), dGTP (400 μM), and dUTP (800 μM). Another dNTP mixture contained dATP-SPh-NPP (400 μM) instead of dATP. The final concentration of DNA target was 400 cp/reaction.

TaqMan® PCRs of equal composition were positioned on two separate sections of a 96-well plate. Each section contained PCR mixtures with regular dNTPs and PCR mixtures containing dATP-SPh-NPP. Each PCR was prepared as triplicate. One section of the plate was covered with aluminum foil, whereas the other section was exposed to light from an UV-LED lamp (InGaN, Quantum well, $\lambda_{max}$=393 nm, 0.18 W/LED) for 8.0 min. at room temperature. Afterwards the cover was removed and the plate was subjected to PCR amplification cycles and subsequend DNA melting with a LightCycler 480 System. The analysis of PCR growth curves was performed from fluorescence data collected in the Cy5.5 channel, while analysis of melting curves was based on fluorescence data collected in the FAM channel (465-510 nm).

Figure 6:
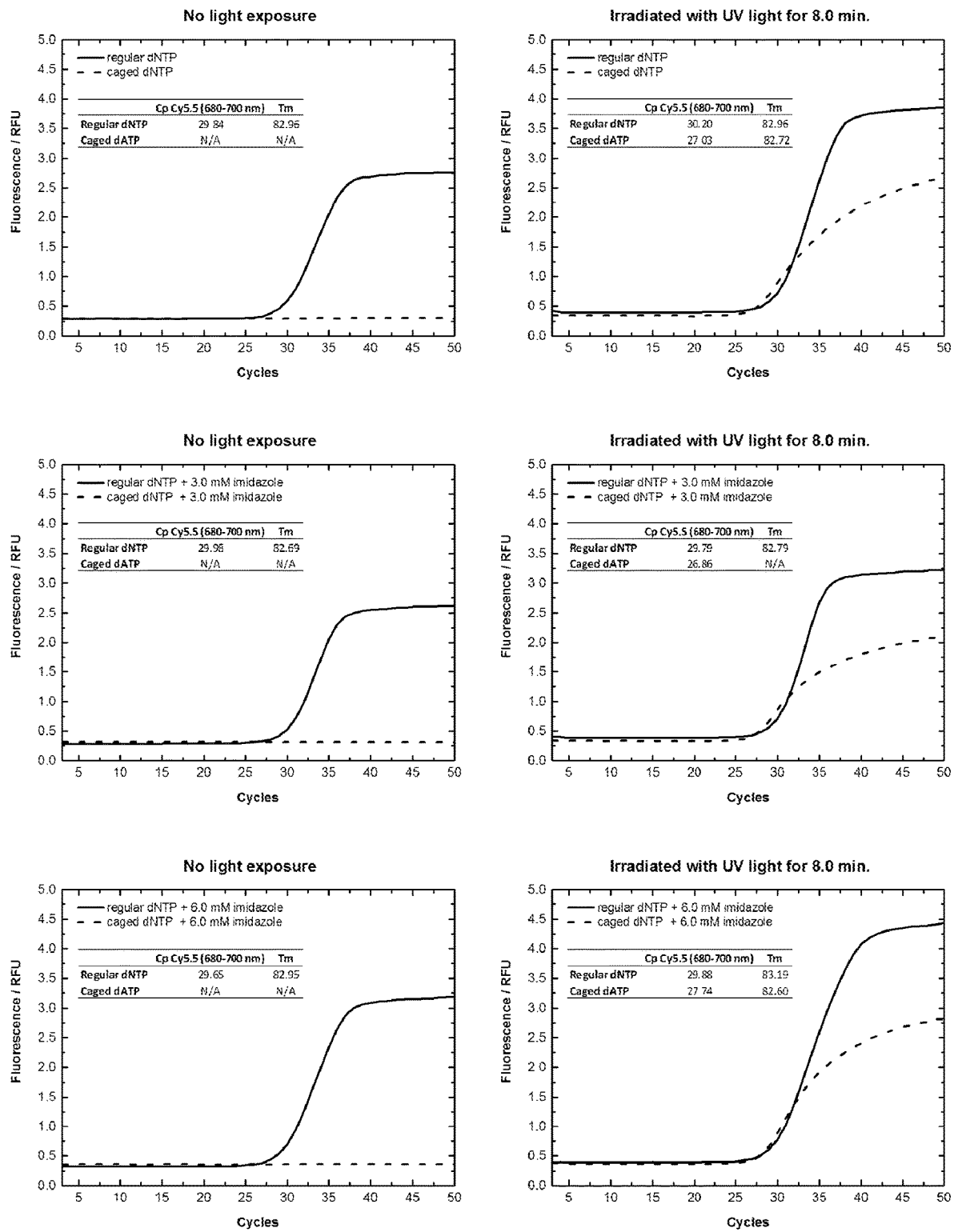
FIG. 6 shows the results of PCR amplification reactions performed with regular dGTP, dCTP, dUTP and caged dATP-SPh-NPP without (graphs on left column) and with (graphs on right column) exposure to UV light for 8 minutes.

Result: Caged dATP with SPh-NPP prevents PCR amplification (FIG. 6, graphs on left column; no UV exposure). Irradiation with UV light for 8.0 min. and subsequent PCR cycling leads to DNA amplification (FIG. 6, graphs on right column). The addition of imidazole did not significantly affect the shapes of the PCR growth curves.

The invention claimed is:

1. A method of detecting the presence or absence of a target nucleic acid sequence in a sample comprising:
   a) performing an amplifying step comprising contacting the sample with amplification reagents to produce an amplification product if the target nucleic acid sequence is present in the sample, and
   b) detecting the amplification product,
   wherein the amplification reagents comprise a modified nucleoside triphosphate having a photocleavable moiety and having a structure of:

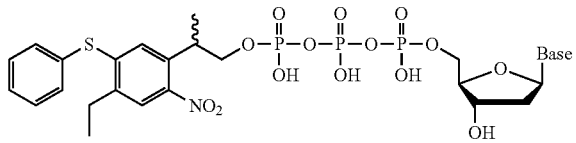

where Base is a purine or pyrimidine base or an analog; and wherein prior to step a), the modified nucleoside triphosphate is irradiated with light having a wavelength capable of cleaving the photocleavable moiety.

2. A method of amplifying a target nucleic acid sequence in a sample comprising:
   providing amplification reagents to perform an amplifying step, wherein the amplification reagents comprise a modified nucleoside triphosphate having a photocleavable moiety and having a structure of:

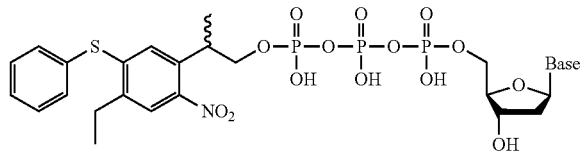

where Base is a purine or pyrimidine base or an analog; and wherein prior to the amplifying step, the modified nucleoside triphosphate is irradiated with light having a wavelength capable of cleaving the photocleavable moiety.

3. A method of reducing or preventing non-specific amplification of nucleic acid in a sample during amplification by polymerase chain reaction (PCR) comprising:
 a) providing amplification reagents that are used to amplify a target nucleic acid, wherein the amplification reagents comprise a nucleic acid polymerase and a modified nucleoside triphosphate having a photocleavable moiety and having a structure of:

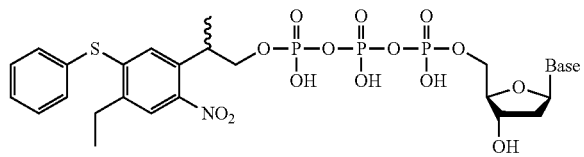

where Base is a purine or pyrimidine base or an analog;
 b) contacting the sample with the amplification reagents at room temperature, whereby the photocleavable moiety on the modified nucleoside triphosphate prevents processing by the nucleic acid polymerase, thereby suppressing formation of non-specific amplification products from room temperature activity of the nucleic acid polymerase;
 c) prior to amplifying, irradiating the modified nucleoside triphosphate with light having a wavelength capable of cleaving the photocleavable moiety to release free nucleoside triphosphate; and
 d) amplifying the target nucleic acid by PCR.

4. A modified nucleoside triphosphate having a photocleavable moiety and having a structure of:

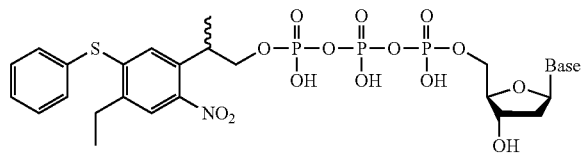

where Base is a purine or pyrimidine base or an analog.

5. The modified nucleoside triphosphate of claim 4 characterized by having greater thermostability compared to an unmodified nucleoside triphosphate.

6. A kit comprising the modified nucleoside triphosphate of claim 4 and further comprising reagents necessary for performing an amplification reaction.

7. A kit comprising the modified nucleoside triphosphate of claim 5 and further comprising reagents necessary for performing an amplification reaction.

* * * * *